United States Patent
Wortmann et al.

(10) Patent No.: US 6,536,199 B2
(45) Date of Patent: Mar. 25, 2003

(54) METHOD AND APPARATUS FOR CONTROLLING A YARN FALSE TWIST TEXTURING MACHINE

(75) Inventors: Thomas Wortmann, Wuppertal (DE); Michael Pyra, Brüggen (DE); Reinhard Lieber, Sprockhövel (DE); Michael Klug, Bochum (DE); Stefan Geissler, Velbert (DE)

(73) Assignee: Barmag AG, Remscheid (DE)

( * ) Notice: Subject to any disclaimer, the term of this patent is extended or adjusted under 35 U.S.C. 154(b) by 0 days.

(21) Appl. No.: 10/060,766

(22) Filed: Jan. 30, 2002

(65) Prior Publication Data

US 2002/0088218 A1 Jul. 11, 2002

Related U.S. Application Data (63) Continuation of application No. PCT/EP01/05687, filed on May 18, 2001.

(30) Foreign Application Priority Data

May 30, 2000 (DE) .......................................... 100 26 942

(51) Int. Cl.⁷ ............................................... D01H 13/32
(52) U.S. Cl. ........................................... 57/264; 57/284
(58) Field of Search ........................ 57/264, 284, 285, 57/286, 287, 288, 289, 290, 291, 292, 332, 333, 350, 265; 700/139

(56) References Cited

U.S. PATENT DOCUMENTS

| | | | |
|---|---|---|---|
| 4,720,702 A | | 1/1988 | Martens |
| 4,720,806 A | | 1/1988 | Schippers et al. |
| 4,809,494 A | * | 3/1989 | Dammann .................... 57/291 |
| 5,394,334 A | * | 2/1995 | Simon ........................... 57/264 |
| 5,515,266 A | | 5/1996 | Meyer |
| 5,517,404 A | * | 5/1996 | Biber et al. .................... 57/264 |
| 5,590,045 A | * | 12/1996 | Kaak et al. .................... 57/264 |
| 6,209,302 B1 | | 4/2001 | Wortmann et al. |
| 2002/0014065 A1 | * | 2/2002 | Pujol .............................. 57/75 |

FOREIGN PATENT DOCUMENTS

| | | |
|---|---|---|
| DE | 30 05 746 A1 | 8/1981 |
| DE | 33 24 243 A1 | 2/1984 |
| DE | 197 10 229 A1 | 11/1997 |
| EP | 0 389 849 A2 | 10/1990 |
| WO | WO 98/33963 A1 | 8/1998 |

* cited by examiner

Primary Examiner—Rodney M. Lindsey
Assistant Examiner—Shaun R Hurley
(74) Attorney, Agent, or Firm—Alston & Bird LLP (57) ABSTRACT

A method and apparatus for controlling a machine for false twist texturing a plurality of synthetic filament yarns and which includes a plurality of side by side processing stations. The plurality of processing stations are divided into a plurality of sections, with each section comprising a plurality of processing stations. The processing stations of each of the sections are monitored and controlled independently of the processing stations of adjacent sections, so that the processing of the yarns in each section is independent of the processing of the yarns in adjacent sections.

22 Claims, 6 Drawing Sheets

METHOD AND APPARATUS FOR CONTROLLING A YARN FALSE TWIST TEXTURING MACHINE

CROSS REFERENCE TO RELATED APPLICATION

This application is a continuation of PCT/EP01/05687, filed May 18, 2001, and designating the United States.

BACKGROUND OF THE INVENTION

The invention relates to a method and apparatus for controlling a yarn false twist texturing machine of the type disclosed in WO 98/033963 and corresponding U.S. Pat. No. 6,209,302.

Texturing machines of this kind comprise a plurality of processing stations—normally as many as 216 or more processing stations—which are arranged side by side on one longitudinal side of the machine. Each of the processing stations comprises a plurality of processing units for respectively advancing, texturing, drawing, and winding a yarn to a package. The processing units and, thus, the process steps in the individual processing stations are monitored and controlled via a central machine control unit. For the operation, the control unit normally comprises an operator controllable visual display unit, which permits visualizing and changing control and monitoring data. However, it is also common to use two separate visual display units respectively for controlling and monitoring the process. To be able to intervene in processing steps, a plurality of process controllers are provided, which are all connected to the central machine control unit. It is possible to connect the process controllers to the processing units in two ways. As disclosed in WO 98/033963, it is possible to operate the processing units within a processing station by individual drives with associated controllers, so that a plurality of process controllers are associated to each processing station. In this instance, all process controllers connect to a central machine control unit.

In a second variant, which is disclosed, for example, in DE 33 24 243, processing units of the same function in all processing stations are operated by a central drive, so that all processing units of the same function can be controlled by one process controller. In this variant, the expenditure for the control system is considerably reduced in comparison with the foregoing variant with individual drives, however, with the disadvantage that all processing stations of the texturing machine must be operated synchronously.

It is therefore an object of the invention to provide a method of controlling a texturing machine for false twist texturing a plurality of synthetic filament yarns in a corresponding plurality of processing stations as well as such a texturing machine, wherein a high flexibility is accomplished in the processing of the yarns with a simultaneously little expenditure for the control system.

SUMMARY OF THE INVENTION

The invention is based on the fact that the texturing machine is divided into a plurality of sections, with each of the sections being controlled independently. Thus, a texturing machine with, for example, a total of 216 processing stations is divided, for example, into a total of 18 sections. With that, each of the sections would comprise 12 processing stations. The processing stations of a section are monitored and controlled independently of the processing stations of adjacent sections. The special advantage of the invention lies in that it is possible to produce with one texturing machine, yarns with different settings in the sections. Furthermore, it is possible to shut down each of the sections independently of the adjacent sections for maintenance and elimination of defects, thereby minimizing a production loss. A further advantage is to be seen in that all sections are jointly supplied from one feed line of supply voltage to the texturing machine. To this extent, it is especially advantageous to connect the sections jointly to a main switch or an emergency switch.

To be able to perform within the section on all processing stations substantially the same process steps, an advantageous further development of the method according to the invention provides for monitoring and controlling all process steps of the section by means of a field control unit associated to the section. To this end, all process-relevant parameters are stored in the field control unit. Likewise, the operating data from the processing stations are continuously supplied to the field control unit. Thus, the field control unit permits an individual monitoring and control of the section.

One advantageous embodiment of the method of the invention provides for individually controlling each process step of one of the processing stations independently of the other process steps of the processing station. In particular, this variant of the method permits operating the process units employed as feed systems in a simple manner at different advancing speeds. Thus, it will be advantageous, when all feed systems have the same advancing speed while threading a yarn in a processing station. Only after the yarn is threaded, will the advancing speeds be made different, which leads to a drawing of the yarn.

A particularly great flexibility in processing the individual yarns within a section of the machine is accomplished by a variant of the method wherein the process steps of a processing station are individually controlled irrespective of the process steps of adjacent processing stations.

However, there is also the possibility of controlling as a group the process steps of adjacent processing stations—in particular those of the same function—independently of the other process steps of the processing station. Thus, for example, for unwinding the yarns from a feed yarn package, it is possible to jointly activate the first feed systems of a section.

A further development of the method according to the invention is especially suited for operating the different kinds of process steps within a processing station with the least possible control resources. In this instance, the intended processing steps include, for example, advancing, heating, drawing, twisting, and winding. Thus, it would be possible to control with advantage the process steps as a group, which are performed for advancing the yarn. Contrary thereto, it is preferred to individually control the process steps for twisting a yarn.

In the case that process steps of a plurality of processing stations of a section are combined to a group, a further development of the method is especially advantageous for enabling a shutdown of the process steps independently of the control. Such a shutdown becomes necessary, for example, in the case of a yarn break within a processing station, or when a continuously monitored parameter within a processing station is exceeded.

The method of the present invention is based on a texturing machine with a very large number of processing stations, so that within a section at least six yarns, preferably at least twelve yarns are simultaneously processed in parallel, side-by-side relationship.

The texturing machine of the present invention represents the solution to the underlying object in terms of an apparatus. To this end, the plurality of processing stations are divided into a plurality of sections, each section comprising a plurality of processing stations. Associated to each section is one of several field control units for controlling and monitoring the processing stations of the section. The process controllers for controlling the processing units of the processing stations of a section connect to their associated field control unit. Each section with its associated field control unit thus forms a partial machine, which is to be operated individually. In this connection, the process parameters are predetermined by the field control unit.

To operate the texturing machine, the field control units connect independently of one another to a microprocessor, so that an operator is able to display the data of one of more field control units, or to input or change data on an operator-controllable visual display unit.

To increase the efficiency of a texturing machine, it is further proposed to adapt the microprocessor for being coupled via a line data network to a diagnosis station, thereby enabling a fast intervention by a central station upon occurrence of a defect.

To transmit data between the field control unit and the process controllers, as well as between the process controllers and the field control unit, it is advantageous to provide a serial bus system. With that, it is possible to quickly perform adjustment changes.

Based on different requirements of individual process steps, the amount and frequency of the data exchange between the processing units and the field control unit are different. To this end, the bus system may advantageously consist of a plurality of data networks, which have different data transmission rates.

To be able to make individual adjustment changes in the process steps of the processing stations, an advantageous further development of the texturing machine according to the invention provides for associating an individual one of the process controllers to each of the processing units of the processing stations pertaining to one section.

Within the processing stations, which contain no major changes, the process steps may advantageously be realized by dividing the processing units of the processing stations of a section into groups of the same function, and an individual process controller is associated to each group of processing units.

To maintain the flexibility in the processing of yarns despite combining individual process steps of adjacent processing stations to groups, a further development of the texturing machine provide for associating a switch to at least one portion of the processing units, by which the processing units are switchably connected to one of the process controllers, the switch being activatable independently of the process controller.

However, such a texturing machine is also suited by itself for solving the problem underlying the present invention. As a result of activating the processing units in groups, the switchable connection between the processing units and the process controllers permits individually activating with advantage each of the processing stations. For example, when a yarn lap occurs in one feed system of a group of jointly controlled feed systems, it will be possible to shut down the affected feed system by the process controller, without influencing the adjacent feed systems in their activation.

The switches provided between the processing units and the process controllers may advantageously be activated by the overriding field control unit.

However, it is also possible to associate to the processing units a monitoring unit, which activates the switches in a case of need.

To be able to shut down a processing unit quickly and without major delay, when need arises, an advantageous further development provides for a sensor arrangement for monitoring at least one parameter of the processing unit. The sensor arrangement connects to the monitoring unit associated to the processing unit or to the field control unit associated to the processing unit. For example, it is possible to select as parameters the temperature of a motor, which a temperature sensor measures directly on the motor, or a desired rotational speed of a drive, which a speed sensor measures directly on a drive. However, it is also possible to trigger the shutdown directly by a signal of the field control unit or monitoring unit, which occurs as a result of a signal from a yarn detector.

Advantageously, the control functions and the monitoring functions are performed by an operator from an operator-controllable visual display unit, the latter being connected to the microprocessor. However, it is also possible to perform the control functions and the monitoring functions from two separate visual display units.

According to a preferred further development of the invention, the sections include each at least six processing stations, preferably twelve processing stations.

BRIEF DESCRIPTION OF THE DRAWINGS

In the following, both the method of the invention and several embodiments of the texturing machine according to the invention are described in greater detail with reference to the attached drawings, in which.

DETAILED DESCRIPTION OF THE PREFERRED EMBODIMENTS

Figure 1:
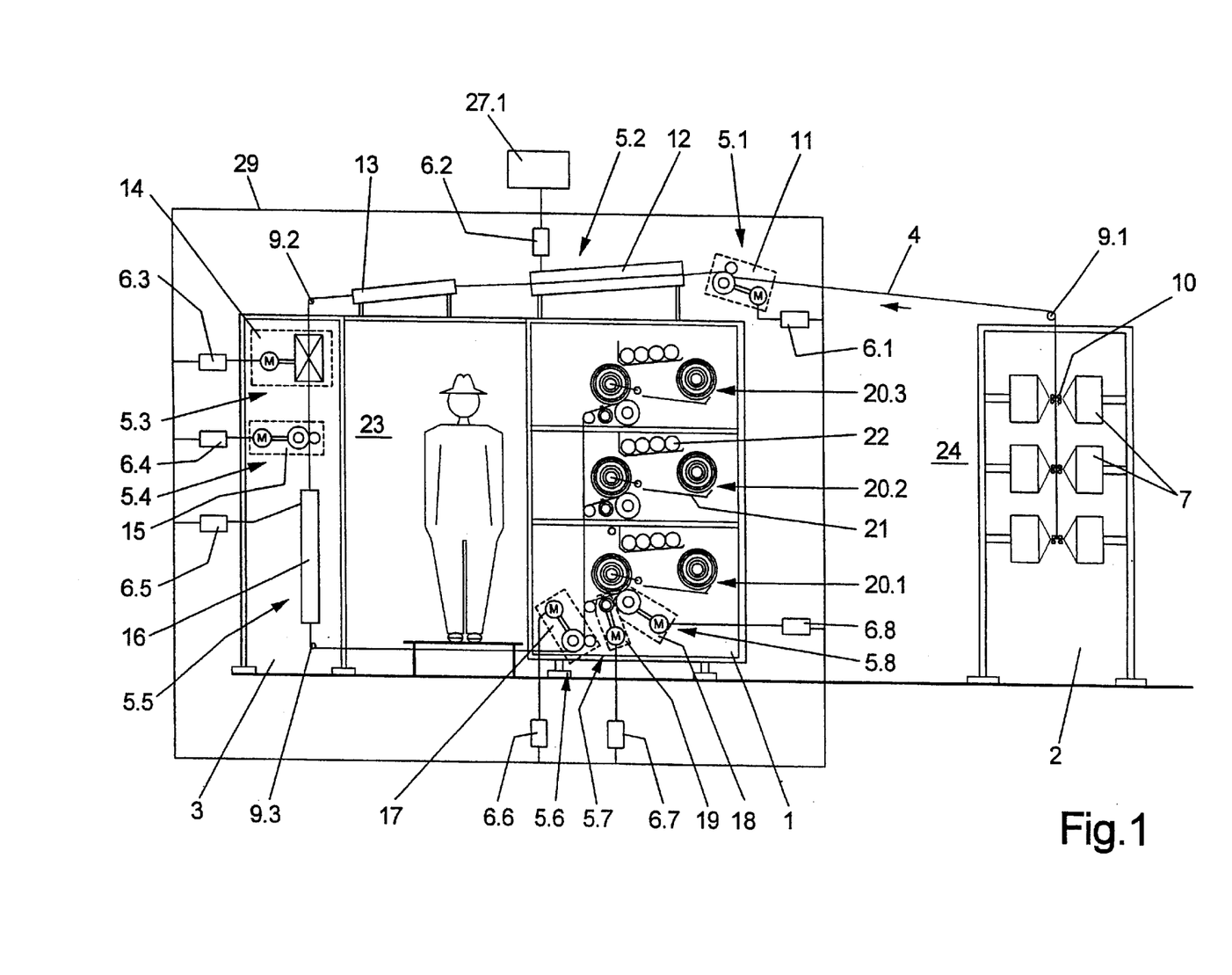
FIG. 1 is a schematic side view of a first embodiment of a texturing machine according to the invention.
Figure 2:
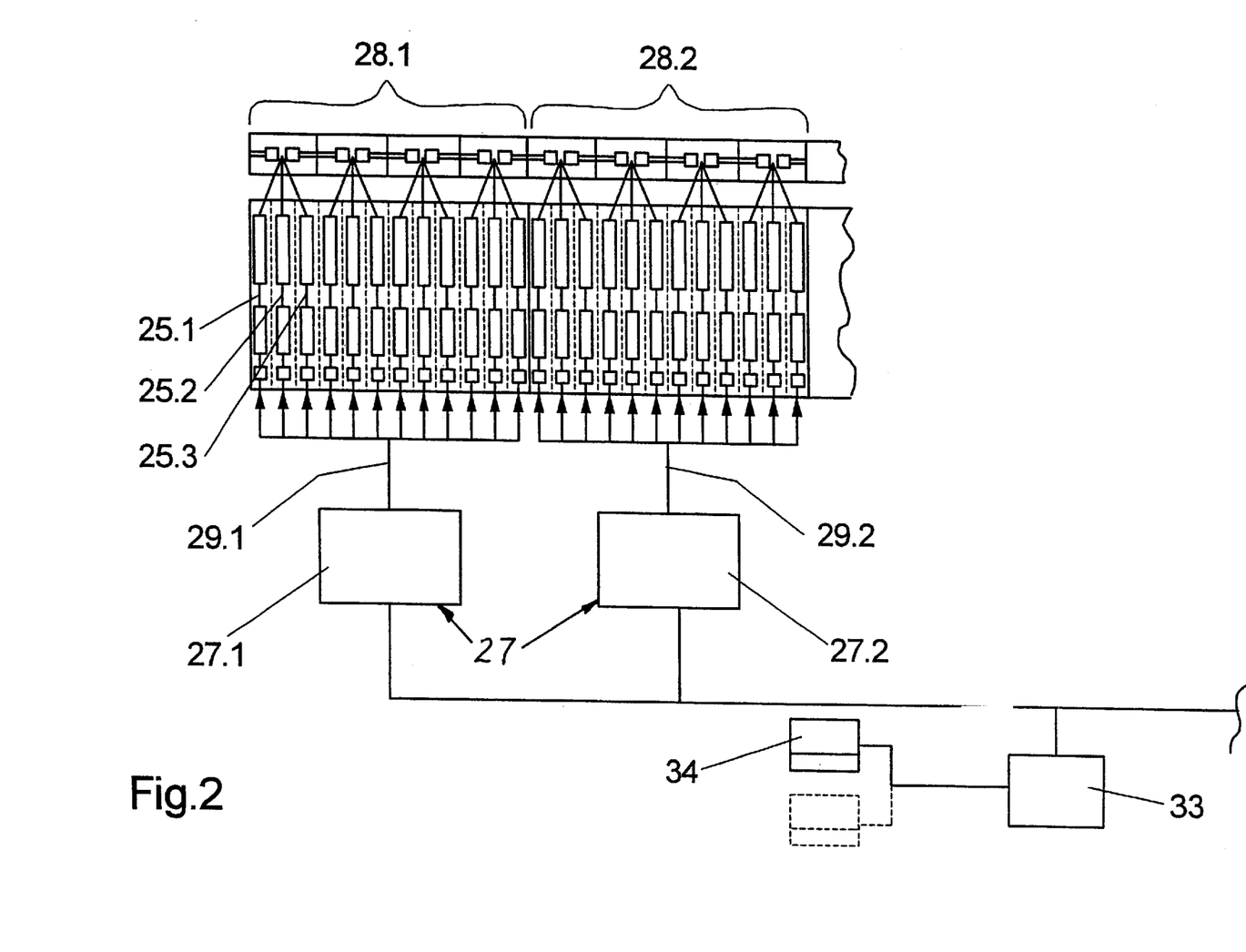
FIG. 2 is a schematic top view of the embodiment of FIG. 1.

FIG. 1 is a schematic side view of a texturing machine according to the invention, and FIG. 2 is a schematic top view of the texturing machine according to the invention. Unless express reference is made to one of the Figures, the following description will apply to both Figures.

The texturing machine consists of a creel frame 2, a process frame 3, and a takeup frame 1. Between the process frame 3 and the takeup frame 1, a service aisle 23 is formed. On the side of the takeup frame 3 opposite to service aisle 23, the creel frame 2 is arranged at a distance from takeup frame 1. With that, a doffing aisle 24 is formed between the takeup frame 1 and creel frame 2.

In the longitudinal direction, the texturing machine comprises a plurality of processing stations 25. Normally, a texturing machine has more than 200 processing stations, of which FIG. 2 illustrates by way of example the first three processing stations indicated at numerals 25.1, 25.2, 25.3.

Each of the processing stations 25 processes one yarn. The takeup units occupy a width of three processing stations. Consequently, respectively three takeup units 20.1, 20.2, 20.3 are arranged in one column in takeup frame 1, with one takeup unit overlying the other, as will be described further below.

Each processing station 25 includes one feed yarn package 7, on which a thermoplastic filament yarn 4 is wound. The yarn 4 is treated and wound to a package in a plurality of process steps by a plurality of processing units 5.1–5.8, which are successively arranged in the direction of the advancing yarn. Associated to each of processing units 5.1–5.8 is a process controller 6.1–6.8. The process controllers 6.1–6.8 are coupled, via a bus system 29, with a field control unit 27.1.

Individually, the processing units of the texturing machine shown in FIGS. 1 and 2 are formed by a first feed system 11, a heater 12, a false twist texturing unit 14, a second feed system 15, a set heater 16, a third feed system 17, a yarn traversing device 19, and a package drive 18. In a processing station 25, the first feed system 11 unwinds the yarn 4 under a certain tension via a yarn guide 10 and a deflection roll 9.1. The first feed system 11 includes a motor and a feed shaft connected to the motor. The feed shaft may be designed and constructed, for example, as a feed roll with a zigzag yarn guide track on its circumference, as disclosed in WO 98/033963. However, it is also possible to construct the feed shaft as a godet, about which the yarn loops several times. Irrespective of the construction of the feed shaft, an electric motor is respectively provided for its drive. Thus, the process controller 6.1 for controlling the motor is designed and constructed as a frequency changer.

In the direction of the advancing yarn, downstream of first feed system 11, a first elongate heater 12 extends, through which the yarn 4 advances. In so doing, the yarn is heated to a certain temperature. The heater could be constructed as a high-temperature heater, in which the heater surface temperature is more than 300° C. Such a heater is known, for example, from EP 0 412 429, which is herewith incorporated by reference. To control the temperature, the heater 12 is associated with process controller 6.2, which is designed and constructed in this instance as a heat control system.

Downstream of heater 12 is a cooling rail 13. The cooling rail 13 is followed by a false twist unit 14 in process frame 3. This false twist unit 14 may be designed and constructed as a friction disk unit with an individual motor drive as disclosed in EP 0 744 480. Associated to the motor of false twist unit 14 is process controller 6.3, for example, a frequency changer.

Downstream of false twist unit 14, a second, further feed system 15 is used to pull the yarn 4 both over heater 12 and cooling rail 13. The second feed system 15 is controlled via process controller 6.4. The feed system 15 could be constructed in the same way as the previously described first feed system 11.

Located downstream of second feed system 15, when viewed in the direction of the advancing yarn, is a set heater 16, which is likewise associated with a process controller 6.5. The set heater 16 is followed by the further, third feed system 17, which advances the yarn 4 from heater 16 to takeup unit 20.1. Associated to feed system 17 is process controller 6.6. The takeup unit 20.1 is arranged in takeup frame 1. In the takeup unit 20.1, the yarn is wound to a package. The package is driven by package drive 18 at a substantially constant circumferential speed. To this end, the package drive includes a drive roll, which is in direct contact with the circumference of the package. The drive roll is operated by a motor, which is coupled with process controller 6.8. Before contacting the package, the yarn 4 is reciprocated by traversing device 19, so that a cross wind forms on the package. Likewise, the traversing device includes a drive, which is activated by process controller 6.7.

The takeup unit 20.1 includes a package storage 21, which serves to receive full packages, when a full package has been produced on the takeup unit. For removing a full package, a spindle support is pivoted, and the full package is deposited in package storage 21. In the package storage 21, the full package waits for its removal. For this reason, the package storage 21 is arranged on the side of the takeup frame 1, which adjoins doffing aisle 24 and faces away from service aisle 23. Furthermore, each takeup unit 20 is equipped with a tube feed device 22, which not described in greater detail.

Likewise, adjacent processing stations 25.2, 25.3, etc. include the above-described processing units 5.15.8. As shown in FIG. 2, the processing stations are successively arranged in a longitudinal direction. The plurality of processing stations of the texturing machine are divided into a plurality of sections 28.1, 28.2, etc. Shown in FIG. 2 are two complete sections 28.1 and 28.2. The sections 28.1 and 28.2 include a plurality of processing stations. In the present embodiment, twelve juxtaposed processing stations 25 form one section 28. To each section 28, a field control unit is associated, so that section 28.1 is controlled by field control unit 27.1, and section 28.2 by field control unit 27.2. In this case, the process controllers 6.1–6.8 of processing stations 25 of one section connect to their respectively associated field control unit 27 via a bus system. In the present embodiment, field process control unit 27.1 connects via bus system 29.1 to process controllers 6.16.8 of section 28.1. The field process control unit 27.2 connects via bus system 29.2 to process controllers 6.16.8 of section 28.2. All processing stations of the texturing machine are divided in this way.

The field control units 27.1 and 27.2 are coupled with a microprocessor 33, which enables, for the purpose of operation, both a data display and data change to each of the field control units 27. To this end, the microprocessor 33 connects to an operator-controllable visual display unit 34. In the cases, wherein a separate operation for controlling and monitoring the sections is desired, it would also be possible to connect microprocessor 33 to two separate visual display units.

In the texturing machine shown in FIGS. 1 and 2, all processing stations of section 28.1 are monitored and controlled by field control unit 27.1 independently of the processing stations of adjacent sections 28.2 etc. Each section forms a partial machine, which may be operated independently of the adjacent section. Only the energy supply to the sections (not shown) occurs from a central interface, since the texturing machine connects to one feed line of supply voltage. Likewise devices, such as, for example, the compressed-air supply system for removing waste yarn by suction, are supplied from a central interface.

Figure 3:
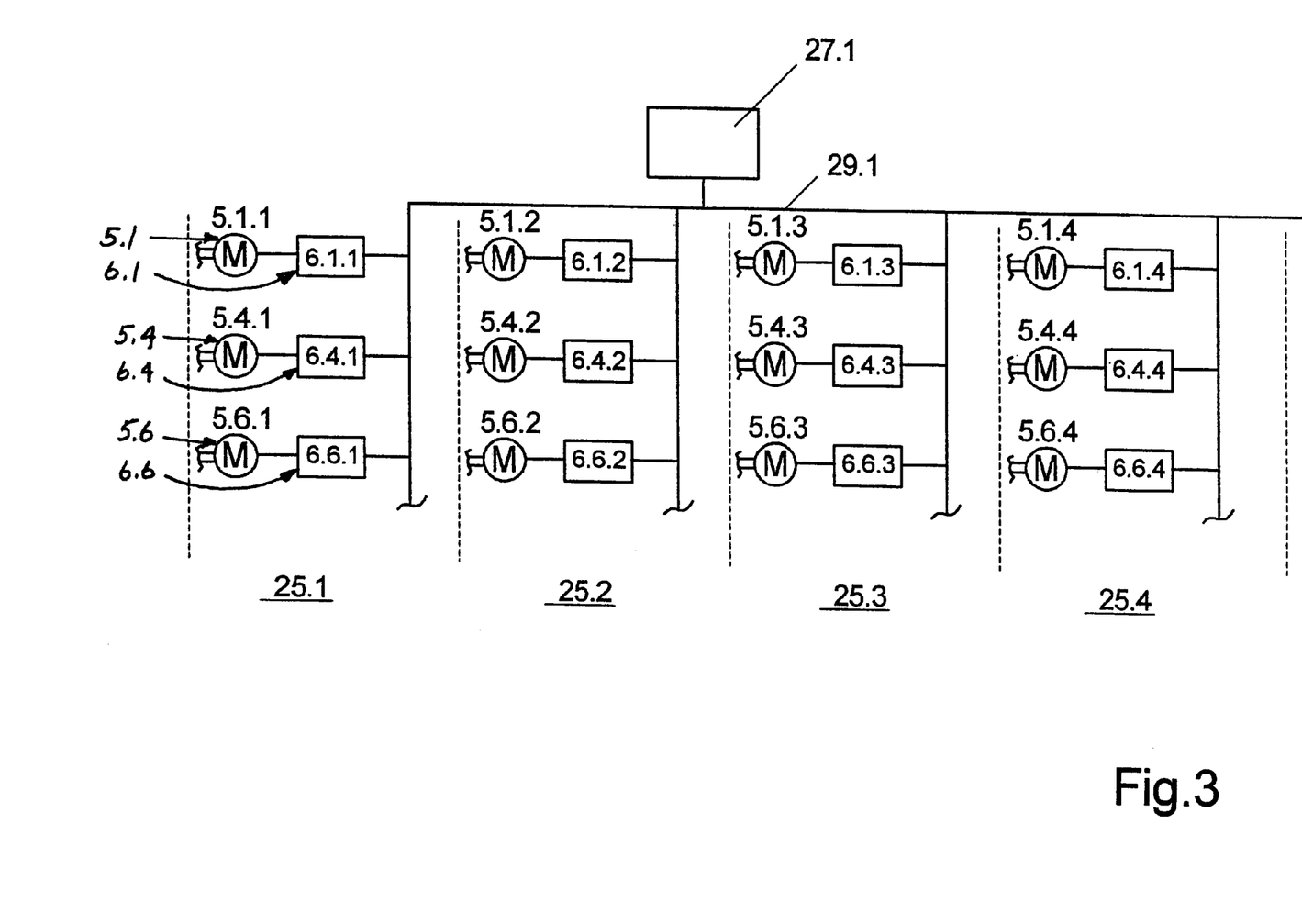
FIG. 3 is a schematic view of a control system of a section of the texturing machine of FIGS. 1 and 2.

FIG. 3 schematically illustrates the coupling between the process controllers of the processing stations of one section with a field control unit, as is realized in the texturing machine of FIGS. 1 and 2, the Figure showing for each processing station 25 only a portion of the processing stations of the section and only a portion of the processing units of a processing station. As an example, four processing stations 25.1, 25.2, 25.3, and 25.4 are selected. For advancing and drawing the yarn, each processing station includes a total of three processing units 5.1, 5.4, and 5.6, which are designed and constructed as feed systems 11, 15, and 17. For the sake of clarity, the schematic in FIG. 3 shows only the drives of the processing units. Thus, processing station 25.1 includes processing units 5.1.1, 5.4.1, and 5.6.1. Likewise, processing station 25.2 includes the same processing units 5.1.2, 5.4.2, and 5.6.2. The processing units associated to processing stations 25.3 and 25.4 are arranged in an analogous manner. Associated to each processing unit 5.1 is respectively one individual process controller 6.1, so that in processing station 25.1, the processing unit 5.1.1 is coupled with process controller 6.1.1. In a corresponding manner, the processing unit 5.4.1 is coupled with process controller 6.4.1, and processing unit 5.6.1 with process controller 6.6.1. The other processing stations 25.2, 25.3, and 25.4 are likewise constructed in such a manner that each processing unit 5 is coupled with a dedicated process controller 6. In the illustrated embodiment, five drives are selected as processing units, so that the process controllers 6 could be formed by frequency changers.

All process controllers 6.1, 6.4, and 6.6 of processing stations 25.1, 25.2, 25.3, and 25.4 are coupled via bus system 29.1 to field control unit 27.1. With that, it is possible to individually activate each of the processing units of each of the processing stations.

Figure 4:
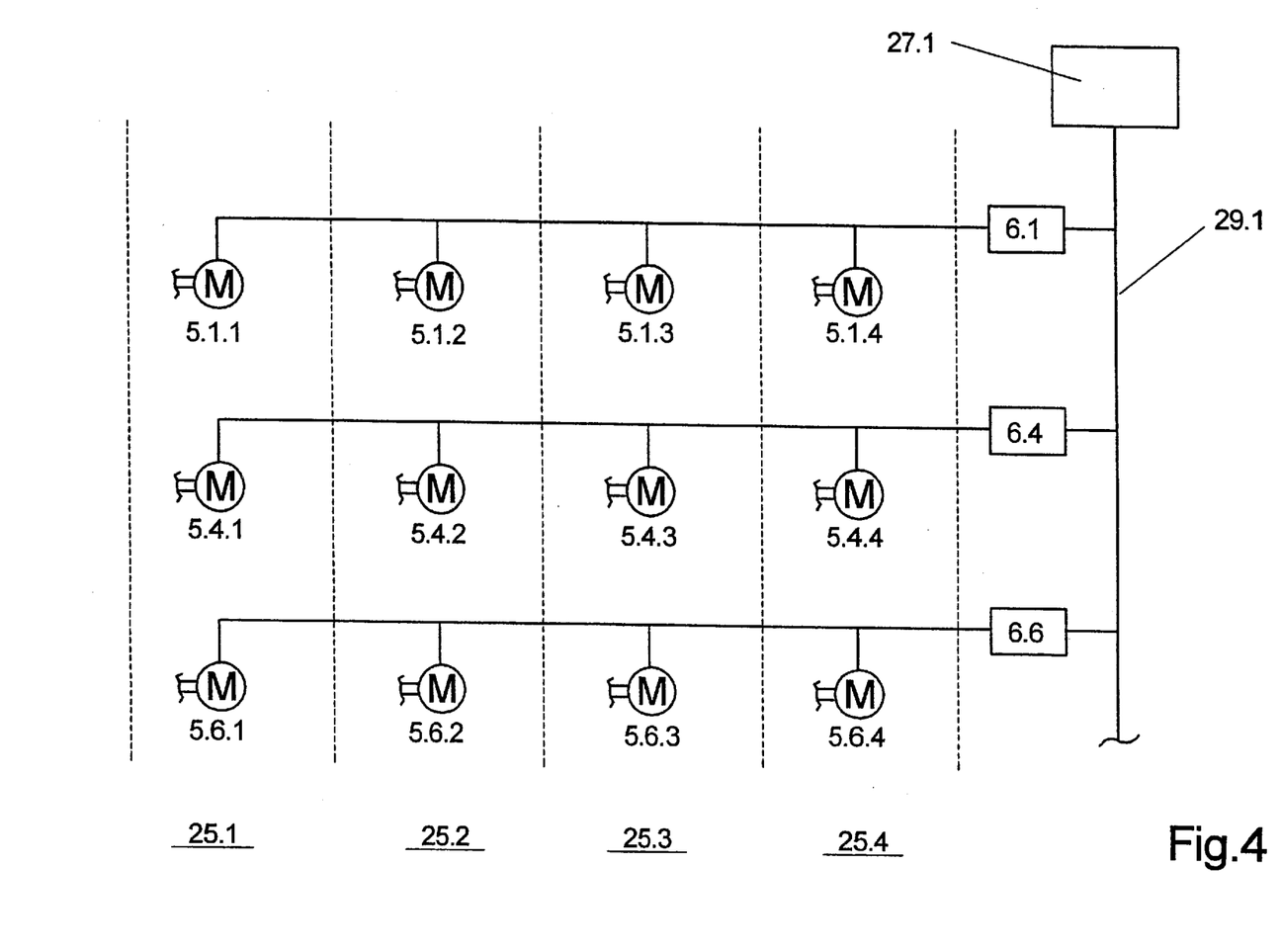
FIG. 4 is a schematic view of a further embodiment for activating a section of the texturing machine according to the invention.

FIG. 4 schematically illustrates a further embodiment for activating the processing units within a section, the section being controlled by field control unit 27.1. Shown as an example are only four processing stations 25.1, 25.2, 25.3, and 25.4 of the section, with the drives of feed systems 11, 15, and 17 having again been selected, for example, as processing units. Thus, processing station 25.1 comprises processing units 5.1.1, 5.4.1, and 5.6.1, and processing station 25.2 processing units 5.1.2, 5.4.2, and 5.6.2. The further processing stations are realized in a corresponding manner. The processing units 5.1.1, 5.1.2, 5.1.3, and 5.1.4 of processing stations 25.1, 25.2, 25.3, and 25.4 are combined to a group and jointly activated via process controller 6.1. Likewise, the processing units 5.4 of processing stations 25.1, 25.2, 25.3, and 25.4 are combined to one group and coupled with process controller 6.4. The processing units 5.6 of all processing stations connect to process controller 6.6. Via bus system 29.1, the process controllers 6.1, 6.4, and 6.6 connect to field control unit 27.1. Such a coupling of the processing units is advantageous, in particular for drives of the processing stations, which are operated at the same speed. The process controllers 6.1, 6.4, and 6.6 thus represent a group frequency changer, which controls all connected drives in like manner.

Figure 5:
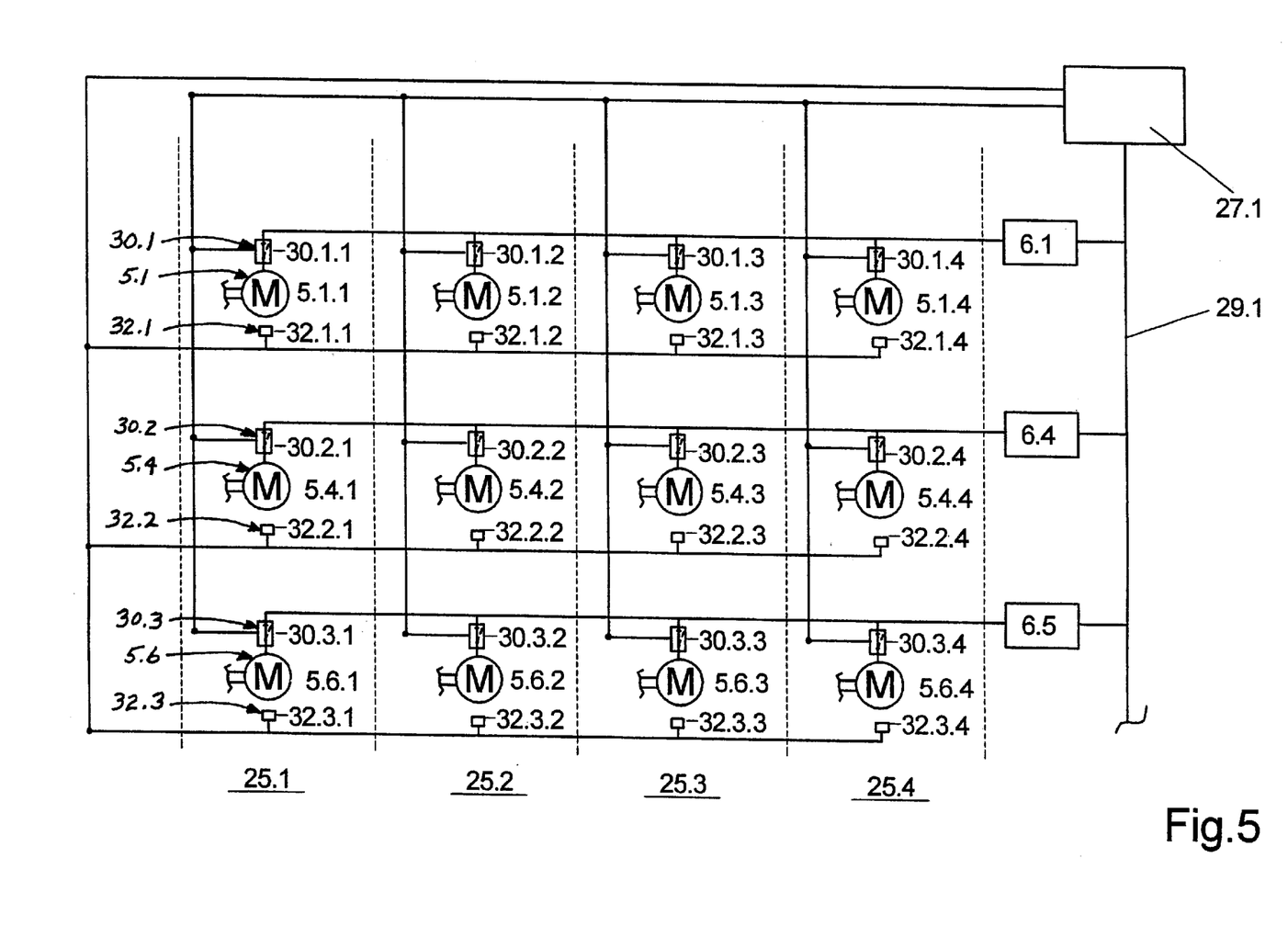
FIGS. 5 and 6 are views of further embodiments for activating a section of the texturing machine according to the invention.
Figure 6:
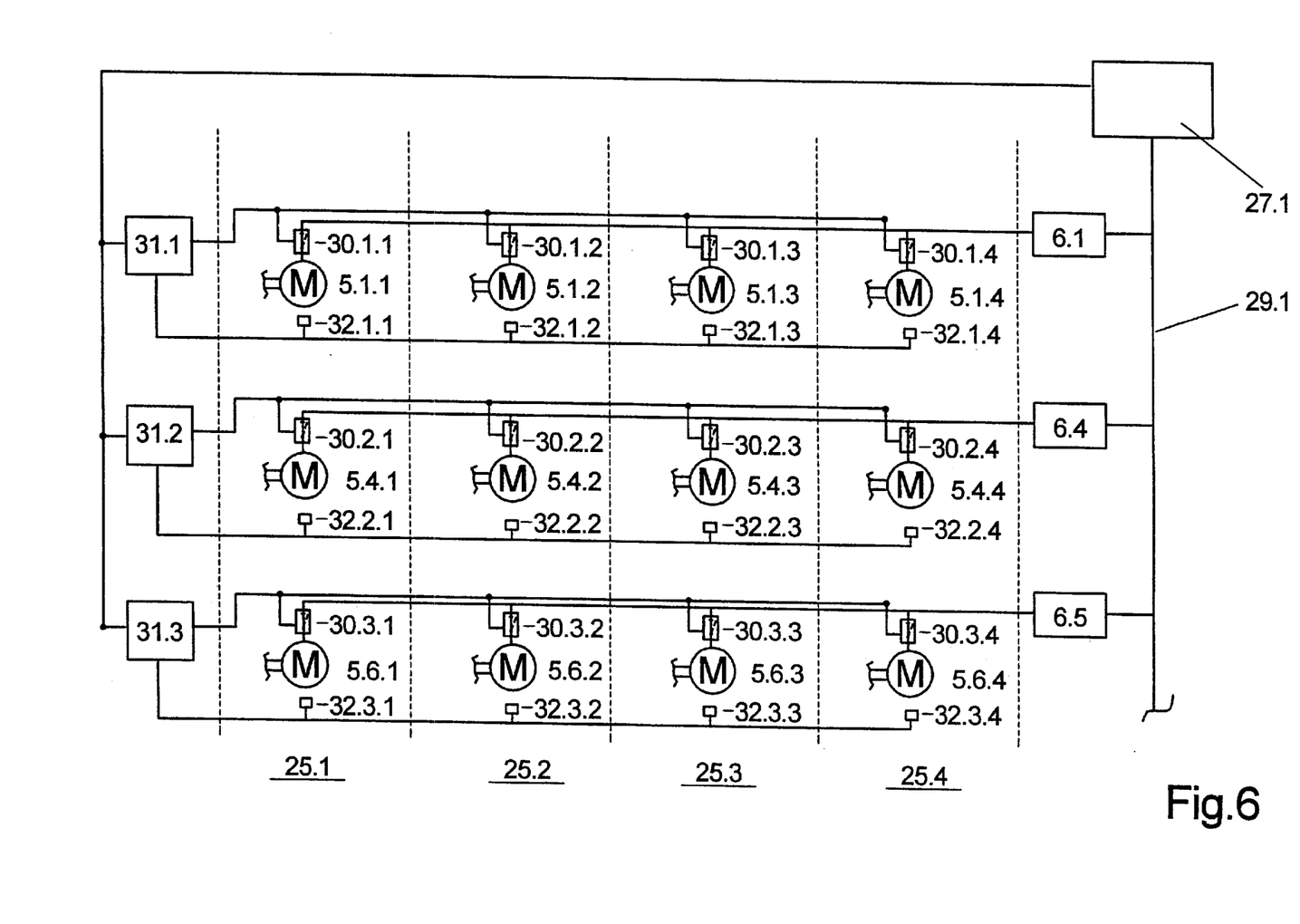

FIGS. 5 and 6 schematically illustrate further examples of coupling and monitoring the processing units of a section with a field control unit. The embodiment shown in FIG. 5 is identical with the coupling shown in FIG. 4. To this extent, the foregoing description is herewith incorporated by reference and only the differences are described in the following.

The processing units 5.1 of processing stations 25.1–25.4 are jointly connected to process controller 6.1, with a switch 30.1 being associated to each processing unit 5.1. The switch 30.1 permits interrupting the connection between process controller 6.1 and the respective processing unit 5.1. To this end, the switch 30.1 is activated directly by field control unit 27.1. Associated to each of the processing units 5.1 is a sensor arrangement 32.1, which connects to field control unit 27.1. In the same way, a switch 30.2 and a sensor arrangement 32.2 are associated to processing units 5.4 in processing stations 25.1, 25.2, 25.3, and 25.4. Likewise, the processing units 5.6 of the four processing stations 25.1, 25.2, 25.3, and 25.4 are each coupled via a switch 30.3 to process controller 6.6. Furthermore, the processing units 5.6 are associated with sensors 32.3.1–32.3.4.

In the embodiment of the texturing machine according to the invention as shown in FIG. 5, at least one parameter in processing unit 5 is monitored via the sensor arrangement 32. This may be, for example, a monitoring of the rotational speed, or a monitoring of the temperature. The actually measured data are supplied by sensor arrangement 32 to field control unit 27.1. In the case that one of the processing units 5 shows an unacceptable parameter value, the field control unit 27.1 will activate switch 30.1, which is associated to processing unit 5. Thus, the affected processing unit 5 is immediately decoupled from process controller 6. This permits eliminating, for example, yarn breaks in one processing station without affecting adjacent processing stations, which are associated to the same controller.

FIG. 6 illustrates a further embodiment of a control device with a group control. The setup and arrangement of the units correspond substantially to the setup of the schematic shown in FIG. 5, 50 that the foregoing description is herewith incorporated by reference. Other than in the embodiment shown in FIG. 5, the switches 30.1.1–30.1.4 of adjacent processing stations 25.1–25.4 connect to a monitoring unit 31.1. Likewise, the sensor arrangements 32.1.1–32.1.4 of adjacent processing stations 25.1–25.4 are linked to monitoring unit 31.1. The monitoring unit 31.1 stores desired parameters of the individual processing units 5.1.1–5.1.4. As soon as one of the sensors 32.1 signals a deviating parameter, the switch 30.1 associated to processing unit 5.1 will be activated. The control and monitoring of processing units 5.4 and 5.6 proceed in the same way. Associated to processing units 5.4 is monitoring unit 31.2, and to processing units 5.6 monitoring unit 31.3. For purposes of both exchanging data and receiving overriding commands, the monitoring units 31.1, 31.2, and 31.3 connect to field control unit 27.1.

In the above described embodiments of the texturing machine according to the invention, the number of processing stations within a section is exemplary. Thus, it is easy to combine six, eight, ten, or even more processing stations to one section. Advantageously, the sections may also be formed by selecting predetermined separations in the creel frame as reference for selecting the number of processing stations. Thus, it is known that creel frames are formed by a plurality of movable units, each of the units holding, for example, twelve feed yarn packages. In this instance, a section corresponds to a creel gauge.

Likewise, the number and the construction of processing units are exemplary. The texturing machine may comprise, for example, only two feed systems, with the takeup unit following directly the second feed system. However, it is also possible to provide a plurality of feed systems as processing units, so that, for example, between the false twist unit and the set heater two feed systems follow each other, between which a further processing unit is arranged for entangling the yarns. Regardless of the realization of the processing units and process controllers, the method of the present invention and the texturing machine of the present invention distinguish themselves in that a plurality of processing stations are divided into few sections and can be controlled as small units in a simple manner.

What is claimed is:

1. A method of controlling a texturing machine for false twist texturing a plurality of synthetic filament yarns and which includes a plurality of adjacent processing stations of generally like construction, comprising the steps of dividing the plurality of processing stations into a plurality of sections, with each section comprising a plurality of processing stations, and monitoring and controlling the processing stations of each of the sections independently of the processing stations of adjacent sections.

2. The method of claim 1, wherein in each processing station of each section, a yarn is at least advanced, textured, drawn, and wound by a plurality of process steps, and that all process steps of the section are monitored and controlled by a field control unit associated with the section.

3. The method of claim 2, wherein each process step of each of the processing stations is individually controllable irrespective of the other process steps of the processing station.

4. The method of claim 2, wherein the process steps of each of the processing stations are individually controllable and monitored irrespective of the process steps of adjacent processing stations of the section.

5. The method of claim 2, wherein at least some of the like process steps of adjacent processing stations of each section are controllable as a group independently of he other processing steps of the processing stations of the section.

6. The method of claim 2, wherein the process steps of the processing stations of each section are controlled in part individually and in part as a group.

7. The method of claim 5, wherein the monitoring and controlling step of the method includes shutting down one of the like process steps of a group independently of the other process steps of the group.

8. The method of claim 7, wherein the shutdown of one of the process steps of the group occurs as a function of a continuously monitored parameter.

9. The method of claim 1, wherein in the processing stations of one of the sections, at least six yarns are simultaneously textured in a parallel, side-by-side relationship.

10. A texturing machine for false twist texturing a plurality of synthetic filament yarns comprising a plurality of processing stations, with each processing station comprising a plurality of processing units for respectively advancing, texturing, drawing, and winding an advancing yarn, a plurality of process controllers which are associated with the processing units of the processing stations, and wherein the plurality of processing stations are divided into a plurality of sections, with each section comprising a plurality of processing stations, and a plurality of field control units associated with respective ones of the sections for controlling and monitoring the processing stations of the associated section, and wherein the process controllers of the processing stations of each section are connected to the associated field control unit.

11. The texturing machine of claim 10, wherein the field control units are each separately connected to a microprocessor for displaying, inputting, and/or changing data.

12. The texturing machine of claim 11, wherein the microprocessor is coupled via a line data network to a diagnosis station.

13. The texturing machine of claim 10, wherein the field control units connect independently of one another, via a serial bus system, to the associated process controllers.

14. The texturing machine of claim 13, wherein the bus system is formed from a plurality of data networks with different data transmission rates.

15. The texturing machine of claim 10, wherein a n individual one of the process controllers is associated with each of the processing units of the processing stations of a section.

16. The texturing machine of claim 10, wherein the processing units of the processing stations of a section are divided into groups of the same function, and that an individual one of the process controllers is associated to each group of processing units.

17. The texturing machine of claim 10, wherein the processing units of the processing stations of a section are associated in part individually to one of the process controllers and in part in groups to one of the process controllers.

18. The texturing machine of claim 10, wherein a switch is associated with at least some of the processing units, by which such processing units are connected via the switch to one of the process controllers, and wherein each switch is activatable independently of the process controller.

19. A texturing machine for false twist texturing a plurality of synthetic filament yarns, comprising a plurality of processing stations, with each station comprising a plurality of processing units for respectively advancing, texturing, drawing, and winding an advancing yarn, a plurality of process controllers each connected to the like processing units of the processing stations, a switch associated with each processing unit for selectively connecting each processing unit with its associated process controller, and a field control unit for actuating the switches independently of the associated process controller.

20. The texturing machine of claim 19, wherein each switch is activatable by a monitoring unit connected to the associated process controller, the monitoring unit being connecting to the field control unit which overrides the process controller.

21. The texturing machine of claim 20, further comprising a sensor arrangement for monitoring at least one parameter of each processing unit, and wherein each sensor arrangement connects to the monitoring unit associated with the processing unit, or to the field control unit associated with the processing unit.

22. The texturing machine of claim 19, wherein the field control unit is connected to a microprocessor for inputting, and/or changing data, with said microprocessor being connected to at least one operator controllable visual display unit.

* * * * *